(12) United States Patent  
Nielsen et al.

(10) Patent No.: US 7,856,079 B2  
(45) Date of Patent: Dec. 21, 2010

(54) RECONSTRUCTION METHOD FOR COMPUTER TOMOGRAPHY AND COMPUTER TOMOGRAPH

(75) Inventors: Tim Nielsen, Hamburg (DE); Michael Grass, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 417 days.

(21) Appl. No.: 11/719,304

(22) PCT Filed: Nov. 7, 2005

(86) PCT No.: PCT/IB2005/053636

§ 371 (c)(1),
(2), (4) Date: May 15, 2007

(87) PCT Pub. No.: WO2006/051468

PCT Pub. Date: May 18, 2006

(65) Prior Publication Data

US 2009/0074133 A1    Mar. 19, 2009

(30) Foreign Application Priority Data

Nov. 15, 2004  (EP)  .................................. 04105782

(51) Int. Cl.
*A61B 6/00*   (2006.01)
(52) U.S. Cl. .................................. 378/19; 378/4; 378/8
(58) Field of Classification Search .................. 378/4, 378/8, 19
See application file for complete search history.

(56) References Cited

U.S. PATENT DOCUMENTS

| | | | | |
|---|---|---|---|---|
| 5,053,958 A | * | 10/1991 | Tam | 378/4 |
| 5,170,439 A | * | 12/1992 | Zeng et al. | 382/131 |
| 5,706,325 A | * | 1/1998 | Hu | 378/4 |
| 5,867,555 A | * | 2/1999 | Popescu et al. | 378/16 |
| 5,997,883 A | * | 12/1999 | Epstein et al. | 324/306 |
| 5,999,587 A | * | 12/1999 | Ning et al. | 378/4 |
| 6,243,437 B1 | | 6/2001 | Hu et al. | |
| 6,324,247 B1 | * | 11/2001 | Besson | 378/15 |

(Continued)

FOREIGN PATENT DOCUMENTS

JP        2003190143 A   *   7/2003

OTHER PUBLICATIONS

Andersen, A. H., et al.; Simultaneous Algebraic Reconstruction Technique (SART): A superior implementation of the art algorithm; 1984; Ultrasonic Imaging; 6:81-94.

(Continued)

*Primary Examiner*—Edward J Glick
*Assistant Examiner*—Alexander H Taningco

(57) ABSTRACT

It is an object of the invention to provide spiral computer tomography which has a high image quality. It relates to a reconstruction method for computer tomography of the heart, wherein the image is reconstructed from a data component of recordings of a partial detector path of a detector device and from a data component of recordings of a full detector path of the detector device, and to a computer tomograph having a beam source, a drive arrangement for driving the beam source in a spiral path around an object, a detector device for recording the radiation from the beam source which passes at least partially through the object, and a control device for reconstructing data components of a partial detector path and a full detector path.

20 Claims, 2 Drawing Sheets

U.S. PATENT DOCUMENTS

Figure 1:
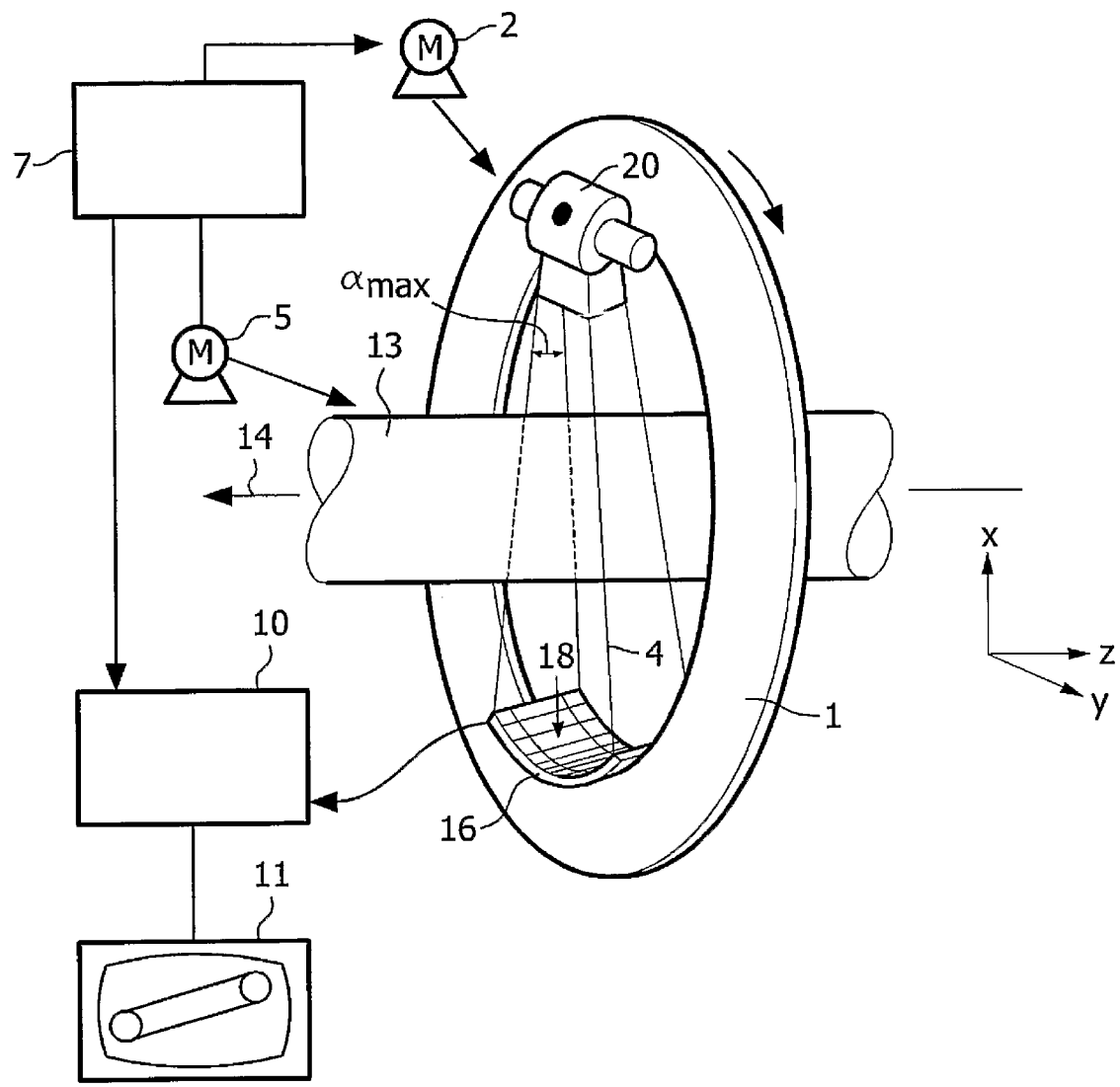

| | | | |
|---|---|---|---|
| 6,480,560 | B2 | 11/2002 | Hsieh |
| 6,504,892 | B1 * | 1/2003 | Ning .............................. 378/4 |
| 6,504,894 | B2 * | 1/2003 | Pan et al. ....................... 378/8 |
| 6,507,633 | B1 * | 1/2003 | Elbakri et al. .................. 378/8 |
| 6,507,639 | B1 * | 1/2003 | Popescu ..................... 378/108 |
| 6,526,117 | B1 | 2/2003 | Okerlund et al. |
| 6,639,965 | B1 * | 10/2003 | Hsieh et al. .................... 378/8 |
| 6,665,370 | B2 * | 12/2003 | Bruder et al. ................. 378/15 |
| 6,768,782 | B1 * | 7/2004 | Hsieh et al. .................... 378/8 |
| 2002/0150201 | A1 * | 10/2002 | Schomberg .................... 378/4 |
| 2003/0118146 | A1 * | 6/2003 | Shida et al. .................... 378/4 |
| 2004/0102688 | A1 * | 5/2004 | Walker et al. ............... 600/407 |
| 2004/0120446 | A1 | 6/2004 | Londt et al. |
| 2004/0174960 | A1 * | 9/2004 | Hsieh et al. ................. 378/210 |
| 2005/0069081 | A1 * | 3/2005 | Kokubun et al. .............. 378/15 |

OTHER PUBLICATIONS

Gordon, R., et al.; Algebraic Reconstruction Techniques (ART) for Three-dimensional Electron Microscopy and X-ray Photography; 1970; J. Theor. Biol.; 29:471-481.

Li, J., et al.; An Adaptive Filtering Algorithm for Cardiac CT with EKG-modulated Tube Current; 2004; IEEE Nuclear Science Symposium Conf. Record; pp. 3757-3758.

Nielsen T., et al.; Iterative Cardiac Cone-Beam CT Reconstruction; 2004; Proc. of SPIE-Image Processing, vol. 5370; pp. 2003-2014.

* cited by examiner

RECONSTRUCTION METHOD FOR COMPUTER TOMOGRAPHY AND COMPUTER TOMOGRAPH The invention relates to a reconstruction method to obtain images for computer tomography, a computer tomography and computer executable instructions stored on a computer readable storage medium for same.

Besides layer methods in the field of computer tomography, spiral methods are occasionally used in which a beam source and a detector device are moved around an object in a spiral path, or helical path, and the radiation is recorded by a detector device, which will be referred to below as spiral computer tomography. Here, the object is usually a patient to be examined. The spiral path is obtained by moving the beam source circularly around the object which is simultaneously moved inside the circular path, perpendicularly to the plane defined by the circular path. Sometimes, especially to record moving organs such as the heart, only data recorded along the spiral path of the beam source and the detector device, referred to below as the detector path, which reflect the same motion state of the organ are used in order to avoid motion artifacts. Motion artifacts are image errors due to different motion states of the object, in this case a moving organ. During the image reconstruction from the data recorded by a detector device, only incomplete recorded data are therefore used in this case, other recorded data which are acquired in other motion states being filtered out or not used. The recorded data of the detector path are therefore not used for all points of the detector device along its spiral path, but recorded data continue to be used only in certain segments of the detector path and recorded data lying outside the segments do not contribute to the imaging. This method is referred to as gating. Owing to its incomplete data, however, gating is a source of image artifacts.

It is an object of the invention to provide spiral computer tomography which has a high image quality.

It relates to a reconstruction method for computer tomography, wherein the image is reconstructed from a data component of recordings of a partial detector path of a detector device and from a data component of recordings of a full detector path of the detector device, and to a computer tomograph having a beam source, a drive arrangement for driving the beam source in a spiral path around an object, a detector device for recording the radiation from the beam source which passes at least partially through the object, and a control device for reconstructing data components of a partial detector path and a full detector path. It furthermore relates to a computer program for carrying out the recording method.

These and other aspects of the invention are apparent from and will be elucidated with reference to the embodiments described hereinafter. The described embodiments should be understood merely as examples and do not imply any limitation of the protective scope of the invention.

Figure 2:
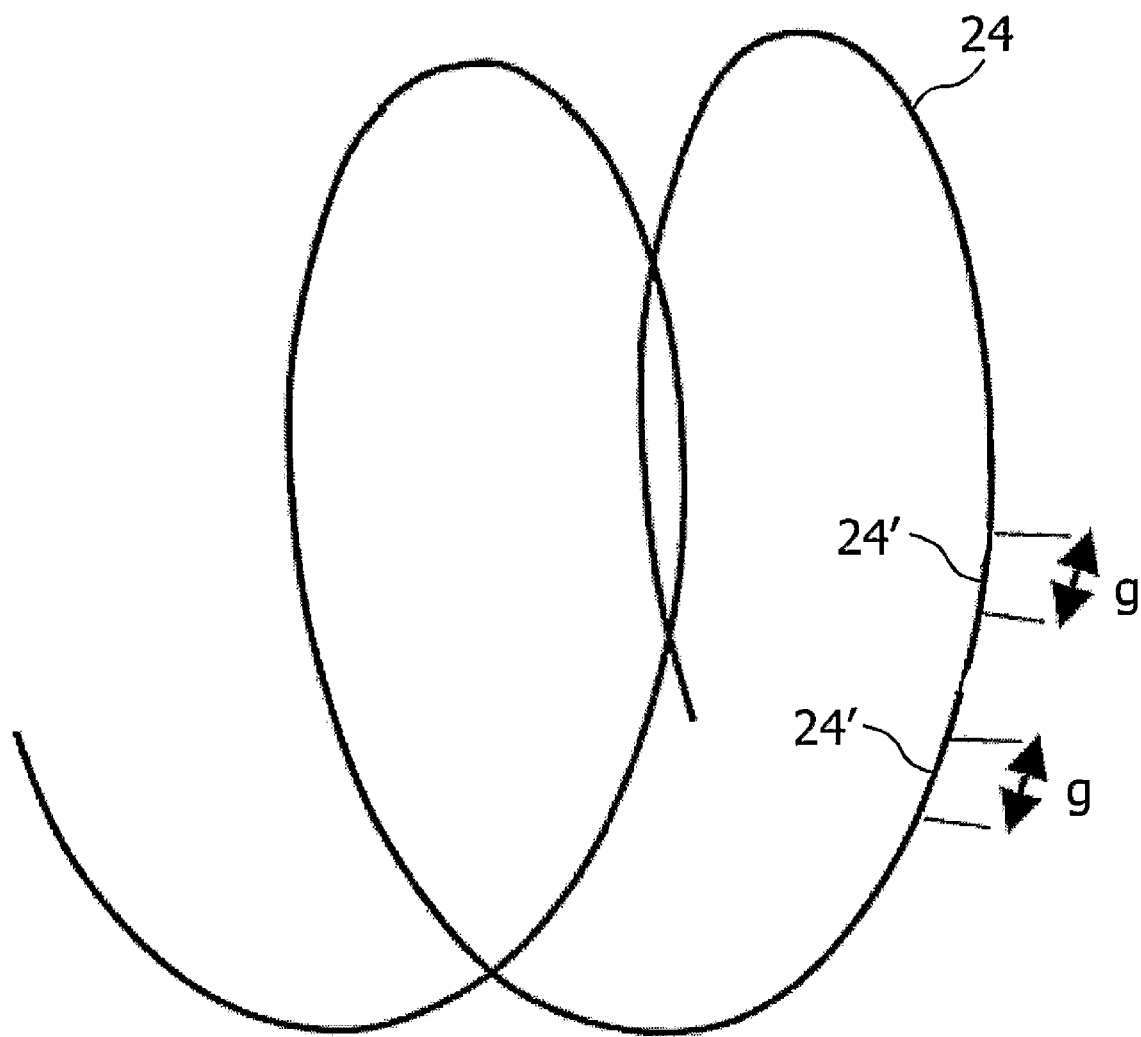

In the drawings:

FIG. 1 shows a schematic representation of a support of a computer tomograph having a beam source, a detector device and an object guided through between the beam source and the detector device, FIG. 2 schematically shows a detector path of a detector device around an object with various sections for the acquisition of recording data.

FIG. 1 shows a schematic representation of a support or gantry 1 which can rotate along the circular path denoted by the curved arrow, parallel to the y direction of the coordinate system represented. To this end, the gantry 1 is driven by a motor 2 with a preferably constant, adjustable angular speed.

Fastened on the gantry 1 there is a beam source 20, for example an X-ray emitter, which comprises a collimator arrangement that emits a cone beam 4 from the radiation generated by the beam source 20. The beam 4 is schematically represented with the aid of four lines which delimit the beam 4. At least some of the cone beam 4 passes through an object 13, which is represented as a section of a cylinder in FIG. 3, the object 13 usually being a patient or a part of a patient on a patient support table. After the rays have passed through the object 13, the beam 4 strikes a detector device 16 fastened on an opposite side of the gantry 1 from the beam source 20, which has a detector surface 18 comprising a multiplicity of detector elements which, in this embodiment, are arranged in rows and columns as a matrix. As the gantry 1 moves, the beam source 20 and the detector device 16 move correspondingly. Each detector element of the detector device 16 which is struck by a ray of the beam 4 delivers a measurement value for the different positions of the mobile beam source 20.

The aperture angle of the beam 4, denoted by the angle $\alpha_{max}$, essentially determines the diameter of the object 13 to be examined, the beam being a cone beam 4.

The object 13 on a patient support table is displaced parallel to the rotation axis 14 of the gantry 1 in the direction of the z axis by a motor 5. The gantry 1 may also be displaced correspondingly in this direction.

If the motors 2, 5 are operating simultaneously, the beam source 20 and the detector device 16 describe a helical trajectory or detector path 24, 24' around the object 13.

The measurement values acquired by the detector device 16 are delivered to a computer device 10 which is connected to the detector device 16, for example via contactless data transmission. The computer device 10 calculates measurement values, reconstructs the distribution of the absorption of the radiation from the radiation source 20 which is essentially due to the object 13, and sends it to an output device 13, usually a monitor. The two motors 2, 5, the computer device 10, the beam source 20 and the transmission of the measurement values from the detector device 16 to the computer device 10 are controlled by a control device 7.

FIG. 2 shows a schematic view of a section of a detector path 24, 24', along which the beam source 20 and the detector device 16 are guided so that the detector device 16 constantly receives the radiation from the radiation source 20, as described above. Driving the beam source 20 and the object 13 respectively by means of the motor 2 and the motor 5 leads to the represented spiral path, or helical path, or trajectory of the beam source 20 around the object 13. Schematically, the full detector path 24 corresponds to the full helical path which comprises a partial detector path 24', two sections of which are denoted by g in FIG. 2. For the sake of representation, only two sections g of the partial detector path 24' are shown here, further sections g being distributed along the full detector path 24 but not represented. The partial detector path 24' consequently forms a part of the full detector path 24, and may also be regarded as a gate or time window. For length ratios of the full detector path 24 to the partial detector path 24', an example which may be mentioned is 60% of the full detector path 24 against 40% of the partial detector path 24', i.e. the sections g in FIG. 2 occupy a 40% proportion of the entire detector path 24. The representation in FIG. 2 is purely schematic and will be explained below. In one embodiment of the invention, a recording is made by means of the detector device 16 along each point of the detector path 24, so as to provide a full data set which comprises the complete recorded data of the object 13 for each point of the full detector path 24, which will be referred to below as a full data component. The computer device 10 then contains data concerning radiation absorbed more or less strongly by the object 13, acquired for various positions along the helical path. The full data component of measurement values acquired by the detector device 16 is delivered to the computer device 10. In the computer device 10, the full data component is converted into a data component which now contains only partial data, so as to provide a partial data component containing measurement values which are acquired by the detector device 16 along the partial detector path 24'. In other words, the part of the data set which is acquired outside the partial detector path 24' on the full detector path 24 is omitted. Then, before reconstruction of the image of the object 13, the computer device 10 contains a full data component acquired by the detector device 16, and a partial data component from reduction of the full data component. This will be referred to as weighting, since the data components are assigned different weights in the computer device 10. As an alternative to converting the data set in the computer device 10, the recordings of the partial detector path 24' may be carried out by modulating the tube current of the X-ray tube of the beam source 20, with a low tube current flowing for the data recording with the full detector path 24 and a high tube current flowing for the data recording with the partial detector path 24'. This measure achieves different weighting of the data components. A combination of the two described features, i.e. converting the data set in the computer device 10 and modulating the tube current of the X-ray tube of the beam source 20, is also feasible. In this case, a high tube current is delivered for the partial detector path 24' and a low tube current is delivered for the full detector path 24, and weighting is additionally carried out between the full data component and the incomplete data component.

In the prior art, either the full data component is used in order to reconstruct the image or the partial data component is used. The first case cannot be employed for moving objects 13 as it would lead to image artifacts, since the recordings acquire different motion states. The term moving objects 13 here refers to independent movements of the object 13, for instance beats of the heart or respiratory motion, independent of the described movement of the object 13 along the z axis and rotation axis caused externally by the motor 5. The second case with a partial data component, also referred to as gating, is therefore employed for moving objects 13 in the prior art with the partial detector path repeatedly acquiring the same motion states of the object 13, and artifacts of the image due to the motion of the object 13 are therefore avoided. Recordings of the same motion states of the heart, for instance with gating, deliver images with approximately the same volume expansion of the heart.

For the purpose of the subsequent image reconstruction from the recorded measurement values, the procedure adopted in the present embodiment is for the full data component to be included to a certain extent in the reconstruction of the images and for the partial data component to be supplementarily included in the reconstruction of the images. This means that not only data components from the regions of the detector path 24 outside the regions denoted by g in FIG. 2 but also data components from inside the regions denoted by g are used for the image reconstruction. This contrasts with the known gating method of the prior art in which only measurement values from inside the regions of the detector path 24 denoted by g, i.e. measurement values which describe the same motion states or phases of the object 13, are used for the image reconstruction. The splitting between the two data components, i.e. the full data component and the partial data component, may be between about 1% to 20% full data component to correspondingly 80% to 99% partial data component, preferably 3% full data component to 97% partial data component. The reconstruction method used to reconstruct images from the measurement values, i.e. the data components, is preferably an iterative reconstruction method in which the image to be reconstructed is projected onto hyperplanes. The hyperplanes are defined by the sum of the contributions of each pixel to the attenuation of a particular X-ray, the ray sum. An image to be corrected is projected onto the first hyperplane, and a correction of the attenuation value of each pixel is computed. The correction is given by the difference between the attenuation value of the object 13 for a particular X-ray path and the computed ray sum of the same X-ray path based on the image to be corrected. This difference is then normalized to the number of pixels which the X-ray path crosses, and added to the running estimate. The iteration method is continued until the difference between a current image projection and the projection of the object 13 falls below a particular value. Essentially, the algorithm projects the initial image to be corrected ray-by-ray into the projection planes, and this projection is compared with the projection of the object 13. A correction based on this difference is projected back in order to define a new image and the iteration is repeated, i.e. a subsequent iteration step is calculated. The algorithms used for the iterative reconstruction method may comprise algebraic reconstruction methods (ART) or simultaneous algebraic reconstruction methods (SART).

An algebraic reconstruction method (ART) is described, for example, in R. Gordon et al. "Algebraic reconstruction techniques (ART) for three-dimensional electron microscopy and x-ray photography" J. Theor. Biol. Vol. 29, pages 471 to 481, 1970, which is incorporated into this description. SART is described, for example, in R. H. Andersen et al., "Simultaneous algebraic reconstruction technique (SART)" Ultrasonic Imaging, Vol. 6, pages 81 to 94, 1994, which is incorporated into this description.

The fundamental idea of ART is based on a discrete representation I of a continuous object function and the calculation of projection data therefrom. The discrete representation I is changed when there is a difference between the calculated and measured projection data of the computer tomograph.

Let the measured projection data p consist of a number X of views p1 . . . pX, an individual view being recorded from a particular point along the helical path of the detector path 24, 24'.

An iteration step k⟼k+1 consists of two operations:

1. For a given view n(k), projection data p' from an estimated image $I_k$ are calculated and compared with the measured data Pn(k). (Projection)

$$p' = P_{n(k)} I_k \qquad (1)$$

$P_{n(k)}$ denotes the projection operator for the view n(k).

2. The estimated image is updated as a function of the observed difference between the measured and calculated projections, which leads to a new estimate $I_{k+1}$. (Back projection)

$$I_{k+1} = I_k + \lambda_{n(k)} \cdot B_{n(k)} (p_{n(k)} - p') \qquad (2)$$

$B_{n(k)}$ denotes the back projection operator for the view n(k).

The value n denotes the order in which the projection data from various views are calculated, formally n: N⟼{1, . . . , X}. λ denotes a weighting factor that controls which component of the observed difference will be projected back to obtain the current image.

Since an iteration step in ART consists of a pair of projection and back projection, the algebraic reconstruction method (ART) is modified in order to use different projections simultaneously. This leads to a simultaneous algebraic reconstruction method (SART), which can be used in this case.

In SART, M projections/back projections are calculated simultaneously or synchronously in each iteration step, formally k↦k+M.

1. Projection data $p'_j$ are calculated from an estimated image $I_k$ and compared with the measured data $p_{n(k+j)}$ for all $j \in [0, \ldots, M-1]$. (Projection)

$$p'_j = P_{n(k+j)} I_k \forall j \in [0, \ldots, M-1] \quad (3)$$

Let $$\Delta_j = \lambda_{n(k+j)}(p_{n(k+j)} - p'_j) \quad (4)$$

2. The estimated image is updated as a function of the observed difference between the measured and calculated projections, which leads to a new estimate $I_{k+M}$. (Back projection)

$$I_{k+M} = I_k + \frac{1}{M} \cdot \sum_{j=0}^{M-1} B_{n(k+j)} \Delta_j \quad (5)$$

The factor 1/M in the back projection step derives from the fact that different views, which are recorded from different angles along the detector path 24, 24', sometimes comprise the same information about the object 13.

Lastly, an example of iterative image reconstruction will be given below, which is carried out with the following formula in the computer unit 10.

$$I(k+1) = I(k) + \lambda_k \kappa_{n(k)} B_{n(k)}(p_{n(k)} - P_{n(k)} I(k)) \quad (6)$$

The term I(k+1) denotes an improved image as described above, i.e. the back projection which is obtained from a current image I(k) with the addition of a correction term made up of the weighting factors λ and κ, with $\kappa_{n(k)}$ occurring only in the Formula (6) used here but not in Formula (2). The weighting factor λ is constant in Formula (6). The weighting factors depend inter alia on the distance of the beam source 20 from the detector device 16 and on the attenuation experienced by the X-rays from the beam source 20 when they travel through the object 13 to the detector device 16. The weighting factor $\kappa_{n(k)}$ furthermore denotes the weighting of the data components, i.e. the weight which is respectively assigned to data of the full detector path 24 and data of the incomplete detector path 24'. The value p denotes projection data which are acquired by the detector device 16 from different positions of the beam source 20, and the coefficient n of the value p describes the individual positions of the beam source 20 along the detector path 24, 24'. The value B denotes the back projection operator, with the coefficient n(k) for each position or view of the beam source 20. The starting value I(k) in the equation above is determined by means of estimation.

The procedure described above avoids image artifacts due to incomplete recordings in the case of gating. Surprisingly, no image artifacts are introduced when the image reconstruction uses recorded data from outside the gate, i.e. data of the full detector path 24, besides the recorded data from inside the gate, i.e. data of the incomplete detector path 24'. The image of the object 13 thereby reconstructed in computer tomography is improved with respect to image artifacts, both compared to the method with a full data component and compared to the method with a partial data component.

The invention claimed is:

1. A reconstruction method to obtain images for computer tomography, comprising:
   reconstructing, via a computing device, an image concurrently from both a data component of recordings of a partial detector path of a detector device and a data component of recordings of a full detector path of the detector device;
   wherein the partial detector path is a sub-set of the full detector path.

2. The reconstruction method as claimed in claim 1, wherein the detector path describes a spiral path around an object to be examined.

3. The reconstruction method as claimed in claim 1, wherein the data component of recordings of the partial detector path has a value in the range of from 80% to 99% and the data component of recordings of the full detector path correspondingly has a value in the range of from 1% to 20%.

4. The reconstruction method as claimed in claim 1, wherein the data component of recordings of the partial detector path is 97% and the data component of recordings of the full detector path is 3%.

5. The reconstruction method as claimed in claim 1, wherein a complete data set is acquired with data of each point of the detector path, and the detector data component of the partial detector path and the data component of the full detector path are derived from the full data set.

6. The reconstruction method as claimed in claim 1, wherein the recordings of the partial detector path are carried out by modulating the tube current of an X-ray tube, a low tube current flowing for the data recording with the full detector path and a high tube current flowing for the data recording with the partial detector path.

7. The reconstruction method as claimed in claim 1, wherein the recordings are taken of the heart or the lung.

8. The reconstruction method as claimed in claim 1, wherein the image reconstruction is carried out by means of an iterative reconstruction method.

9. The reconstruction method as claimed in claim 8, wherein the image recovery is carried out by means of an arithmetic reconstruction method (ART).

10. The reconstruction method as claimed in claim 8, wherein the image recovery is carried out by means of a simultaneous arithmetic reconstruction method (SART).

11. The reconstruction method as claimed in claim 1, wherein the data component of recordings of the partial detector path has a weighted value which is different from the weighted value of the data component of recordings of the full detector path.

12. The reconstruction method as claimed in claim 1, wherein the full detector path-corresponds to one complete revolution of a beam source around an object and the partial detector path is a sub-set of the full detector path corresponding to the one complete revolution.

13. A computer tomograph having a beam source, a drive arrangement for driving the beam source in a spiral path around an object, a detector device for recording the radiation from the beam source which passes at least partially through the object, and a control device for reconstructing data components of both a partial detector path and a full detector path;
   wherein the partial detector path is a portion of the full detector path.

14. The computer tomograph as claimed in claim 13, wherein the control device reconstructs data components of both the partial detector path and the full detector path using an iterative reconstruction method which projects an at least one image onto at least one hyperplane and the at least one hyperplane is the sum of at least one contribution of at least one pixel to an attenuation of at least one radiation ray.

15. The computer tomograph as claimed in claim 13, wherein the control device iteratively reconstructs data components of both the partial detector path and the full detector path until the difference between a current image projection and a previous image projection falls below a predetermined value.

16. A non-transitory computer readable medium encoded with computer executable instructions, wherein the computer executable instructions cause a computing device to perform the following acts:
   reconstruct an image concurrently from both a data component of recordings of a partial detector path of a detector device and from a data component of recordings of a full detector path of the detector device;
   wherein the partial detector path forms a part of the full detector path.

17. The non-transitory computer readable medium encoded with computer executable instructions as claimed in claim 16, wherein the computer executable instructions cause the computing device to reconstruct the image from both the data components using an iterative reconstruction method which projects an at least one image onto at least one hyperplane, wherein the iterations continue until the difference between a current image projection and a previous image projection falls below a predetermined value.

18. The non-transitory computer readable medium encoded with computer executable instructions as claimed in claim 17, wherein the at least one hyperplane is the sum of at least one contribution of at least one pixel to an attenuation of at least one radiation ray.

19. The non-transitory computer readable medium encoded with computer executable instructions as claimed in claim 16, wherein the computer executable instructions cause a computing device to calculate a correction of an attenuation of at least one radiation ray for at least one pixel from both the data components, wherein the correction of the attenuation is the difference between the attenuation of an object for at least one radiation ray path and a computed hyperplane of the at least one radiation ray path.

20. The non-transitory computer readable medium encoded with computer executable instructions as claimed in claim 16, wherein the computer executable instructions cause a computing device to:
   weight the data component of recordings of a partial detector path of a detector device and from a data component of recordings of a full detector path of the detector device with different weighting values; and
   modulate the tube current of an X-ray tube with both a low tube current flowing for the data recording with the full detector path and a high tube current flowing for the data recording with the partial detector path.

\* \* \* \* \*